(12) United States Patent
Robles-Kelly et al.

(10) Patent No.: US 9,373,052 B2
(45) Date of Patent: Jun. 21, 2016

(54) SHAPE AND PHOTOMETRIC INVARIANTS RECOVERY FROM POLARISATION IMAGES

(75) Inventors: Antonio Robles-Kelly, Kaleen (AU); Cong Phuoc Huynh, Braddon (AU)

(73) Assignee: NATIONAL ICT AUSTRALIA LIMITED, Eveleigh, NSW (AU)

( * ) Notice: Subject to any disclaimer, the term of this patent is extended or adjusted under 35 U.S.C. 154(b) by 135 days.

(21) Appl. No.: 13/642,463

(22) PCT Filed: Apr. 20, 2011

(86) PCT No.: PCT/AU2011/000458
§ 371 (c)(1),
(2), (4) Date: Nov. 7, 2012

(87) PCT Pub. No.: WO2011/130793
PCT Pub. Date: Oct. 27, 2011

(65) Prior Publication Data
US 2013/0202214 A1 Aug. 8, 2013

(30) Foreign Application Priority Data

Apr. 21, 2010 (AU) ................................ 2010901672

(51) Int. Cl.
*G06K 9/00* (2006.01)
*G06K 9/46* (2006.01)
(Continued)

(52) U.S. Cl.
CPC *G06K 9/46* (2013.01); *G01N 21/21* (2013.01); *G01N 21/25* (2013.01); *G01N 21/27* (2013.01);
(Continued)

(58) Field of Classification Search
USPC ......... 382/100, 181, 191, 203, 206, 207, 260, 382/325; 356/128, 138, 140, 141.1, 141.2, 356/141.5, 144, 369, 402, 432, 445, 448, 356/601, 612
See application file for complete search history.

(56) References Cited

U.S. PATENT DOCUMENTS 5,028,138 A * 7/1991 Wolff ............................ 356/369
6,987,566 B1 * 1/2006 Smith ........................... 356/369
(Continued)

FOREIGN PATENT DOCUMENTS

WO WO 2009152583 A1 * 12/2009

OTHER PUBLICATIONS

Vimal Thilak, David G. Voelz, and Charles D. Creusere, "Polarization-based index of refraction and reflection angle estimation for remote sensing applications", Applied Optics, vol. 46, No. 30, Oct. 2007, pp. 7527-7536.*
(Continued)

*Primary Examiner* — Eric Rush

(57) ABSTRACT

The disclosure concerns processing of electronic images, such as hyperspectral, or multispectral images. In particular, but is not limited to, a method, software and computer for estimating shape information or a photometric invariant of a location of image of a scene. The image data (300) indexed by wavelength λ and polarization filter angle θ. For each wavelength λ index, a polarization angle φ is estimated from the image data (300) by the processor (810). The processor (810) then also estimates the shape information (such as azimuth α, such as zenith θ, or surface normal) or photometric invariants (such as refractive index) based on the estimated polarization angle φ for each wavelength index λ. Greater accuracies can be achieved in the estimated shape information and/or photometric invariants by using wavelength-indexed data. Further, surface information or photometric invariant can be estimated based upon polarization in a single-view hyperspectral or multi-spectral imagery. Further, by relying on the polarization angle for the estimation, the method is insensitive to changes in illumination power and direction.

7 Claims, 5 Drawing Sheets

(51) Int. Cl.
G06T 7/00 (2006.01)
G01N 21/21 (2006.01)
G01N 21/31 (2006.01)
G01N 21/29 (2006.01)
G01N 21/25 (2006.01)
G01N 21/27 (2006.01)
G06T 17/00 (2006.01)

(52) U.S. Cl.
CPC ............. *G01N 21/29* (2013.01); *G01N 21/31* (2013.01); *G01N 21/3151* (2013.01); *G06T 7/0022* (2013.01); *G06T 7/0051* (2013.01); *G06T 7/0053* (2013.01); *G06T 7/0055* (2013.01); *G06T 7/0073* (2013.01); *G06T 17/00* (2013.01); *G06T 2200/08* (2013.01); *G06T 2207/10016* (2013.01); *G06T 2207/10144* (2013.01)

(56) References Cited

U.S. PATENT DOCUMENTS

| 7,742,168 B2* | 6/2010 | Elton | G01N 21/57 356/369 |
| 2007/0222781 A1* | 9/2007 | Kondo | G06T 15/506 345/426 |
| 2008/0158550 A1 | 7/2008 | Arieli et al. | |
| 2010/0303344 A1* | 12/2010 | Sato et al. | 382/162 |

OTHER PUBLICATIONS

Firooz A. Sadjadi, "Passive three-dimensional imaging using polarimetric diversity", Optical Society of America, Optics Letters, vol. 32, No. 3, Feb. 2007, pp. 229-231.*

Cong Phuoc Huynh and Antonio Robles-Kelly, "Simultaneous Photometric Invariance and Shape Recovery", IEEE, 12th International Conference on Computer Vision, Oct. 2009, pp. 1757-1764.*

Gary A. Atkinson and Edwin R. Hancock, "Shape Estimation Using Polarization and Shading from Two Views", IEEE, Transactions on Pattern Analysis and Machine Intelligence, vol. 29, No. 11, Nov. 2007, pp. 2001-2017.*

Th. Gevers and H. M. G. Stokman, "Robust Photometric Invariant Region Detection in Multispectral Images", International Journal of Computer Vision, vol. 53, Issue 2, Jul. 2003, pp. 135-151.*

Shree K. Nayar, Xi-Sheng Fang and Terrance Boult, "Separation of Reflection Components Using Color and Polarization", International Journal of Computer Vision, vol. 21, Issue 3, Feb. 1997, pp. 163-186.*

Lawrence B. Wolff, "Polarization-Based Material Classification from Specular Reflection", IEEE, Transactions on Pattern Analysis and Machine Intelligence, vol. 12, No. 11, Nov. 1990, pp. 1059-1071.*

Daisuke Miyazaki, Robby T. Tan, Kenji Hara, and Katsushi Ikeuchi, "Polarization-based Inverse Rendering from a Single View", IEEE, Proceedings of the Ninth IEEE International Conference on Computer Vision, vol. 2, Oct. 2003, pp. 982-987.*

Wolff, Lawrence B., "Polarization Vision: a new sensory approach to image understanding", 1997, pp. 81-93.

Frankot, Robert T. et al., "A Method for Enforcing Integrability in Shape from Shading Algorithms", 1988, pp. 439-451.

International Search Report, PCT/AU2011/000458; completion date Jun. 3, 2011; 4 pages.

Written Opinion, PCT/AU2011/000458; completion date Jun. 3, 2011; 4 pages.

Barrois, B. et al., 3D Pose Estimation Based on Multiple Monocular Cues; Computer Vision and Pattern Recognition, 2007; 9 pages.

Atkinson, Gary et al., Recovery of Surface Orientation from Diffuse Polarization; IEEE Transactions on Image Processing 2006; 14 pages.

Thilak, V. et al., Polarization-Based Index of Refraction and Reflection Angle Estimation for Remote Sensing Applications; 2007 Optical Society of America, vol. 46, No. 30; pp. 7527-7536.

Atkinson, Gary et al., Recovery of Surface Orientation From Diffuse Polarization; IEEE Transactions on Image Processing, vol. 15, No. 6; Jun. 2006; pp. 1653-1664.

* cited by examiner

SHAPE AND PHOTOMETRIC INVARIANTS RECOVERY FROM POLARISATION IMAGES

CROSS REFERENCE TO THE RELATED APPLICATION

The present application claims priority from Australian provisional patent application No. 2010901672 filed 21 Apr. 2010 the content of which is incorporated herein by reference.

TECHNICAL FIELD

The disclosure concerns processing of electronic images, such as hyperspectral, or multispectral images. In particular, but is not limited to, a method, software and computer for estimating shape information or a photometric invariant of a location of image of a scene. Examples of processing the image using the estimates include material recognition, shape recovery, recolouring and re-shading of objects represented in the image.

BACKGROUND OF THE INVENTION

FIG. 1(a) illustrates a scene 100 comprising an object 101 having an object surface 102, and a surface normal vector 103. The object surface 102 is illuminated by a light source 110 causing diffuse reflection 111 and specular reflection 112 that are both observed by camera 120. FIG. 1(a) also shows a zenith angle 130 and an azimuth angle 131.

The light source 110 is shown as a wave that oscillates in the two-dimensional plane of the drawing of FIG. 1(a). If a light source consists of only such a wave, it is referred to as parallel-polarised. The wave of the light source 110 may oscillate in a plane perpendicular to the two-dimensional plane of the drawing. In that case, the light source is referred to as perpendicular-polarised.

The wave of the light source 110 may also be a superposition of a parallel and a perpendicular polarised wave. FIG. 1(b) illustrates such a light wave 150 viewed in the direction in which the light travels. The light wave 150 is a superposition of a parallel-polarised wave 151 and a perpendicular-polarised light wave 152. The resulting light wave 150 is therefore tilted by a polarisation angle 153. The ratio of magnitudes of the parallel- and the perpendicular-polarized waves determine the polarisation angle 153.

In FIG. 1(b), the parallel-polarised light wave 151 and the perpendicular polarised light wave 152 have the same wavelength and no phase shift between each other. In other words, the parallel component and the perpendicular component of the light wave 150 are perfectly correlated.

However, the wave may also be unpolarised light, which means that two components are completely uncorrelated and a representation as in FIG. 1(b) is not suitable in that a polarisation angle cannot be determined. The ratio of polarised light to unpolarised light determines a degree of polarisation.

In this technical field transmitted is understood to mean through the surface of the object. According to the Fresnel Equations [1], parallel- and perpendicular-polarised light is reflected and transmitted differently when hitting a surface. With regards to reflection, perpendicular-polarised light is reflected better than parallel-polarised light. With regards to transmission, parallel-polarised light is transmitted better than perpendicular-polarised light. As a result, a larger portion of the parallel-polarised light 110 in FIG. 1(a) is transmitted through the surface 102 than of perpendicular-polarised light. This phenomenon is dependent on the zenith angle 130 and is described quantitatively by the Fresnel Equations.

As indicated by the arrows within the structure of object 101, the transmitted light is reflected several times internally before it is finally emitted through surface 102 to the outside of object 101. Due to the irregular structure of the object, the light emitted from the object 101 is distributed over all directions. This is referred to as diffuse reflection 111.

In one example, the light source 110 emits unpolarised light and the surface 102 only shows diffuse reflection 111 and no specular reflection 112 as the surface is completely matte. When the unpolarised light from light source 110 is transmitted through the surface 102, the light within the structure of the object 101 is still unpolarised. Just before the light of the diffuse reflection is emitted, the light passes through the surface 102 of the object 101. At this point, according to the Fresnel Equations more parallel-polarised light reaches the outside of the object than perpendicular-polarised light. As a result, the light that reaches camera 120 is partially polarised in the direction parallel to the two-dimensional plane of the drawing.

If the object surface 102 is tilted as indicated by the azimuth angle 131, the direction of polarisation of the light that reaches the camera not anymore parallel to the two-dimensional plane of the drawing but rotated by a polarisation angle 153. In fact, the polarisation angle 153 is equal to the azimuth 131 of the surface. As a result, the azimuth 131 of the surface 102 can be determined by determining the angle of polarisation 153.

As mentioned above, the degree of polarisation changes with the zenith angle 130. As a result, the zenith angle 130 can be determined by determining the degree of polarisation.

The azimuth 131 and zenith 130 angles completely define the normal vector 103 of the surface 102. Knowing the normal vector 103 at all points of the surface 102 allows the reconstruction of the shape of the object 101. However, direct measurement of the polarisation angle 153 is inaccurate and the Fresnel Equations are also dependent on the refractive indexon coefficient of the surface, which is unknown in most real world applications.

Any discussion of documents, acts, materials, devices, articles or the like which has been included in the present specification is solely for the purpose of providing a context for the present disclosure. It is not to be taken as an admission that any or all of these matters form part of the prior art base or were common general knowledge in the field relevant to the present disclosure as it existed before the priority date of each claim of this application.

SUMMARY

In a first aspect there is provided a computer implemented method to estimate shape information or one or more photometric invariants of a location of a scene as represented in a hyperspectral or multispectral image data, the image data indexed by wavelength and polarisation filter angle, the method comprising:

(a) for each wavelength index, estimating a polarisation angle from the image data;

(b) estimating the shape information or photometric invariants based on the estimated polarisation angle for each wavelength index.

It an advantage of this method that greater accuracies can be achieved in the estimated shape information and/or photometric invariants by using wavelength-indexed data.

It is a further advantage of the method that surface information or photometric invariant can be estimated based upon polarisation in a single-view multi-spectral imagery. Further, by relying on the polarisation angle for the estimation, the method is insensitive to changes in illumination power and direction.

Step (a) may comprise fitting intensity information of the image data to a function of the filter angle, for example cosine, to estimate the polarisation angle.

Step (b) may further comprise estimating the azimuth of a surface normal of the scene at the location based on the estimated polarisation angle for each wavelength index, and estimating the shape information based on the estimated azimuth. That is, the spectral variation of the phase of polarisation is used to estimate the azimuth.

Step (a) may comprise optimising a difference between intensity information of the image data and a function of the filter angle to estimate the polarisation angle for each wavelength index and determine a residual error for each wavelength index, and step (b) may further comprise estimating the azimuth based on the polarisation angles for each wavelength index weighted by the residual error for each wavelength index.

Step (a) may further comprise estimating a degree of polarisation for each wavelength index based on intensity values, for example maximum and minimum, of the function with reference to the estimated polarisation angle for that wavelength index. That is the wavelength indexed degree of polarisation is based on the Fresnel equation.

Step (b) may further comprise estimating the zenith of a surface normal of the scene at the location based on the estimated degree of polarisation for each wavelength index.

Step (b) may further comprise estimating the photometric invariant of the scene at the location based on the estimated degree of polarisation for each wavelength index.

Step (b) may further comprise optimising a difference between a model and the estimated degree of polarisation for each wavelength index, wherein the model parameters include the zenith and photometric invariant parameters. It is an advantage that the zenith and photometric invariant can be determined simultaneously and that the method does not rely on a predefined value of the photometric invariant.

Optimising the difference between a model and the estimated degree of polarisation for each wavelength index may comprise determining co-efficient of a dispersion equation.

Estimating the photometric invariants may be further based on a constraint over the wavelength index for the photometric invariant. That is, enforcing a wavelength dependent dispersion equation on the photometric invariant makes the problem well posed.

The photometric invariant may be the refractive index.

The method is repeated from each location in the scene represented in the image data. A location is represented in the image data as one or more pixels. The image data may taken from a single view point and/or using an unpolarised light source.

The shape information may comprise a surface normal.

The wavelength index may be comprised of one or more wavelengths used in the image.

In a second aspect there is provided a computer system to estimate shape information or one or more photometric invariants of a location of a scene as represented in a hyperspectral or multispectral image data, the image data indexed by wavelength and polarisation filter angle, the system comprising:

(a) a processor to estimate for each wavelength index a polarisation angle from the image data and to estimate the shape information or photometric invariants based on the estimated polarisation angle for each wavelength index.

The computer may be local to a sensor that captures the image data.

The optional features of the method described above similarly apply to the computer system.

In a third aspect there is provided software, that when installed on a computer causes the computer to perform the method described above.

BEST MODES

Figure 2:
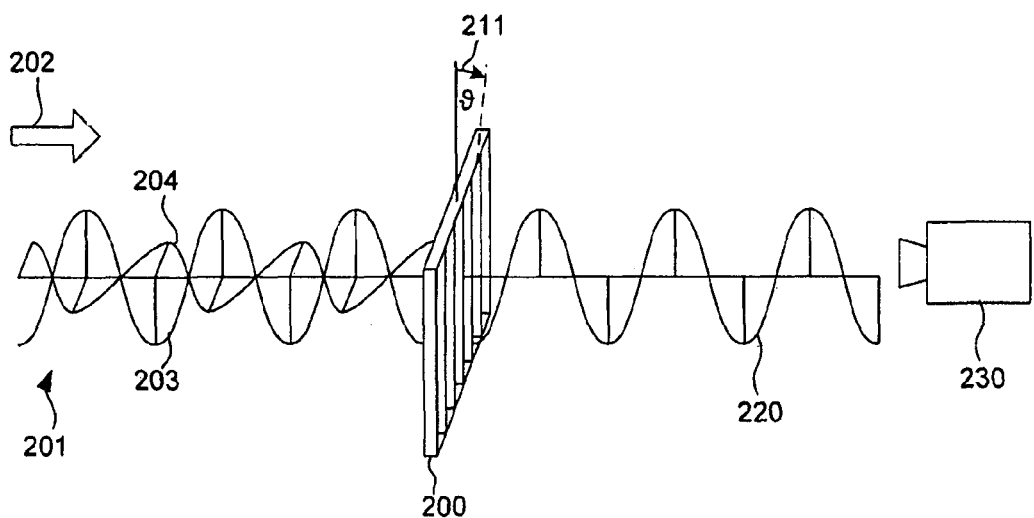

FIG. 2 illustrates the principle of a polarising filter 200. A light wave 201 propagates in direction 202 and enters the filter 200. In this example, the light wave 201 comprises a parallel-polarised light wave 203 and a perpendicular-polarised light wave 204. The filter is rotatable by filter angle θ 211 and the light exits the filter 200 as output light wave 220. A camera 230 captures the output light wave 220.

The filter 200 may be seen as an arrangement of vertical slots. When the light wave 201 enters the filter, only a component with polarisation parallel to the slots will be transmitted through filter 200. In this example, the parallel-polarised light wave 203 is transmitted through filter 200 and exits the filter 200 as parallel-polarised output light wave 220.

When the filter 200 is gradually rotated by filter angle 211 the parallel-polarised light wave 203 is gradually attenuated by the filter 200 and the perpendicular-polarised light wave 204 will be gradually transmitted. At a filter angle of 90 degrees, the parallel-polarised light wave 203 is completely blocked while the perpendicular-polarised light wave 204 is fully transmitted.

Figure 1A:
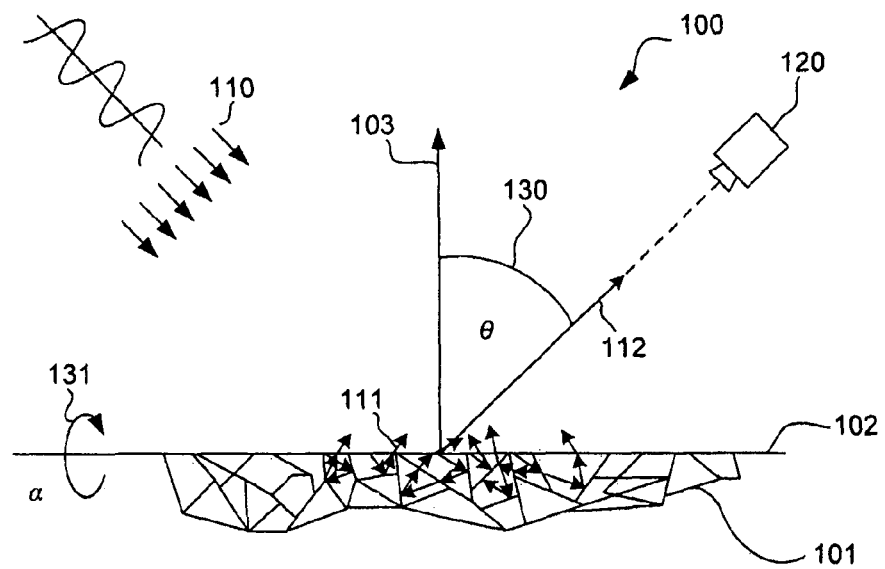
FIG. 1(a) illustrates a scene captured by a camera.
Figure 1B:
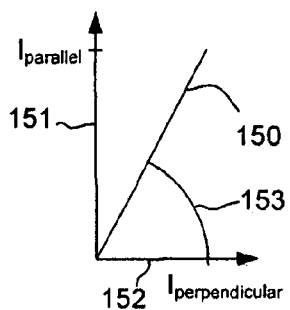
FIG. 1(b) illustrates a superposition of a parallel and a perpendicular polarised light wave. An example will be described with reference to
FIG. 2 illustrates the principle of a polarising filter.

This effect is used in the following where a surface of an object is illuminated by unpolarised light. As described with reference to FIG. 1(a), the light diffusely reflected from surface 102 is partially polarised and the aim is to determine the polarisation angle φ and the degree of polarization ρ of the reflected light.

Figure 4:
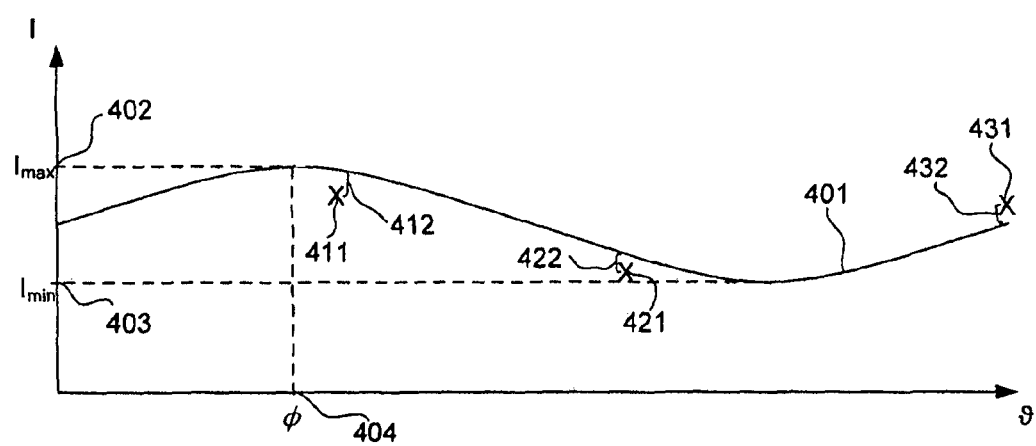
FIG. 4 illustrates the step of determining the polarisation angle for one pixel location $u_1$ and one wavelength $\lambda_1$.

When the output light wave 220 is captured by camera 230, the only information available from the camera is the intensity of the light wave 220. If the parallel-polarised light wave 203 of the input light wave 201 has a higher amplitude than the perpendicular-polarised light wave 204 then a maximal intensity $I_{max}$ will be observed by the camera for a filter angle of θ=0°. Accordingly, a minimal intensity $I_{min}$ will be observed for a filter angle of θ=90°. The intensity between the maximum and the minimum can be described by a cosine function as shown in FIG. 4. The offset of the cosine function is the mean of $I_{max}$ and $I_{min}$ $(I_{max}+I_{min})/2$, and the amplitude is half the difference between $I_{max}$ and $I_{min}$, $(I_{max}-I_{min})/2$. The period of the cosine is $4\pi/2$ or $180°$. In most cases, the dominant component of the input light wave may not be exactly parallel-polarised or perpendicular-polarised but rotated by an angle $\phi$. As a result, the maximum will not be at a filter angle of $\theta=0°$ but of $\theta=\phi$. Therefore, the cosine wave is shifted along the $\theta$ axis by polarisation angle $\phi$. The resulting cosine function for the measured intensity I is $$I(\vartheta) = \frac{(I_{max} + I_{min})}{2} + \frac{(I_{max} - I_{min})}{2}\cos(2\vartheta - 2\phi) \quad (1)$$

The aim is to determine the three unknowns $I_{min}$, $I_{max}$ and $\phi$ from multiple measurements of I at known filter angles $\theta$. There are several alternative methods of determining $I_{min}$, $I_{max}$ and $\phi$ in (1) from a successive sequence of images captured at several filter angles $\theta$. By capturing the same scene with three or more filter orientations, the cosine function can be fitted to the measured intensities using a numerical non-linear least square fitting algorithm. This method is, however, not efficient and especially in case of a large number of pixels this leads to a high computational cost since the optimisation has to be performed per pixel.

Alternatively, these parameters can be obtained making use of the method in [2], where three images at $0°$, $45°$ and $90°$ with respect to a reference axis are acquired so as to compute the phase shift $\phi$, intensity I and degree of polarisation $\rho$. However, the method in [2] is susceptible to noise corruption since it employs only three images. Here, we employ an alternative that yields a stable estimation of the phase shift $\phi$, intensity I and degree of polarization $\rho$ by solving an overdetermined linear system of equations. We commence by rewriting (1) in the following vector form:

$$I_i = \begin{bmatrix} 1 \\ \cos(2\vartheta_i) \\ \sin(2\vartheta_i) \end{bmatrix}^T \begin{bmatrix} \frac{I_{max} + I_{min}}{2} \\ \frac{I_{max} - I_{min}}{2}\cos(2\phi) \\ \frac{I_{max} - I_{min}}{2}\sin(2\phi) \end{bmatrix} = f_i^T x \quad (2)$$

After collecting $N \geq 3$ measurements (i.e. per pixel) at three or more filter angles $\theta$, one arrives at the following overdetermined linear system $$I = Ax \quad (3)$$

where $$I = \begin{bmatrix} I_1 \\ I_2 \\ \vdots \\ I_N \end{bmatrix}$$

and $$A = \begin{bmatrix} f_1^T \\ f_2^T \\ \vdots \\ f_N^T \end{bmatrix}.$$

Equation (3) is well-constrained since the number of equations $N \geq 3$ is no less than the number of unknowns. Moreover, the coefficient matrix A depends solely on the filter angle which allows for an efficient solution of (3). Solving (3) means minimising the difference between the measured intensity I of the image data and the cosine function Having obtained the solution for $x=[x_1; x_2; x_3]^T$, one can recover the maximal intensity $I_{max}$ and minimal intensity $I_{min}$ on the cosine and the phase of polarisation as $$I_{max} = x_1 + \sqrt{x_2^2 + x_3^2}$$
$$I_{min} = x_1 - \sqrt{x_2^2 + x_3^2}$$
$$\phi = \frac{1}{2}\arctan\frac{x_3}{x_2}$$

As discussed above, the maximal intensity on the cosine curve is reached at the polarisation angle $\phi$. Therefore, the azimuth angle $\alpha$ is either the same as the polarisation angle $\phi$ or differs from it by $\pi$ [1], i.e. $\alpha=\phi$ or $\alpha=\phi\pm\pi$. To disambiguate the azimuth angle between the two possibilities, $\phi$ and $\phi\pm\pi$, we assume convexity on the surface under observation. Under this assumption, surface normal vectors point in the opposite direction to that of image gradients. One can determine the azimuth angle as the one between $\phi$ and $\phi\pm\pi$ that yields the closer orientation to the negative gradient direction.

However, due to weak polarisation that causes a drift in polarisation angle $\phi$ estimation, the result of the above method depends on the wavelength $\lambda$ of the light. In order to improve accuracy, the same image is captured at the same filter angle $\theta$ for multiple wavelengths in a multispectral image.

Figure 3:
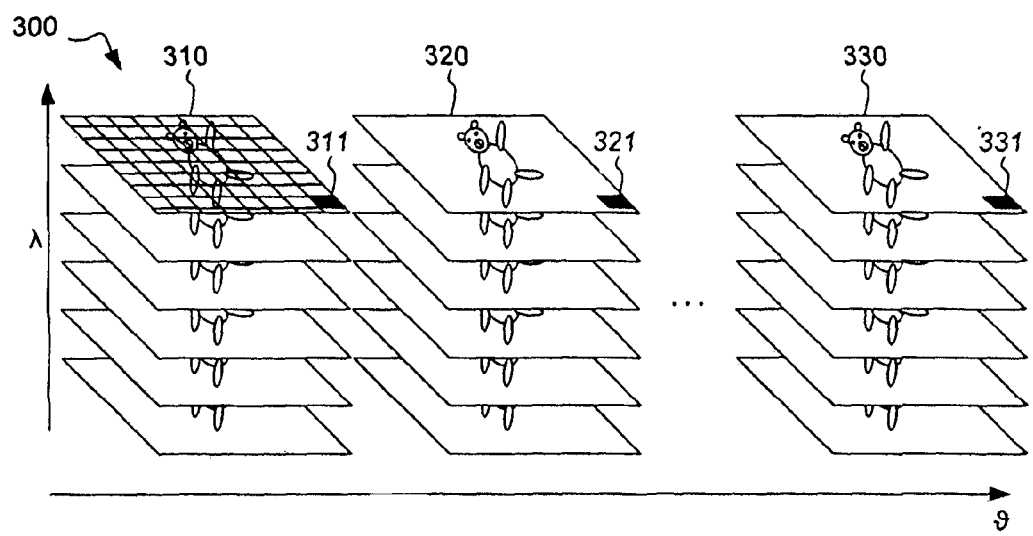
FIG. 3 illustrates wavelength-indexed image data.

FIG. 3 illustrates wavelength-indexed image data 300 of a scene comprising a teddy bear. The image data comprises multiple images 310, 320 and 330. Each of the images 310, 320 and 330 is captured at a different filter angle $\theta$. Each image comprises multiple sub-images indexed by the wavelength $\lambda$. A sub-image is segmented into points, such as pixels. This is shown only for the top sub-image of image 310 but also applies to all other sub-images.

Each pixel has an associated pixel location u within each sub-image. One pixel 311 at location $u_1$ in the top sub-image of image 310 is highlighted. At the same location $u_1$ in the top sub-image of image 320 and 330 are highlighted pixels 321 and 331 respectively.

The following method determines the azimuth $\alpha$ or zenith $\theta$ of the surface normal vector or the refractive index for one pixel location u. The method will be explained in one example of pixel location $u_1$. In order to determine the azimuth $\alpha$ or zenith $\theta$ of the surface normal vector or the refractive index for all pixel locations, the method is simply repeated independently for all other pixel locations.

FIG. 4 illustrates the step of determining the polarisation angle for one pixel location $u_1$ and one wavelength $\lambda_1$. The figure shows the intensity values I and filter angles $\theta$ of three measurements 411, 421 and 431 of pixels 311, 321 and 331 (of FIG. 3), respectively, obtained by camera 120 in FIG. 1(a). In most examples more than three images are taken at different filter angles resulting in more than three intensity values but only three are shown here for simplicity of description.

A cosine function 401 is fitted to the measurements 411, 421 and 431. The fitting usually results in differences 412, 422 and 432 for each of the measurements 411, 421 and 431 respectively. Based on these differences, a residual error $\epsilon$ is determined. This error is quantified as the $L_2$-norm of the residual error $\epsilon$ of (3), $\epsilon=\|I-Ax\|_2$. From the cosine function 401 a maximal intensity $I_{max}$ 402, a minimal intensity $I_{min}$ 403 and the polarisation angle ϕ 404 are determined. Note that these values cannot be determined directly from the measurements 411, 421 and 431 since the measurements most likely do not fall exactly onto the maximum or minimum points.

Figure 5:
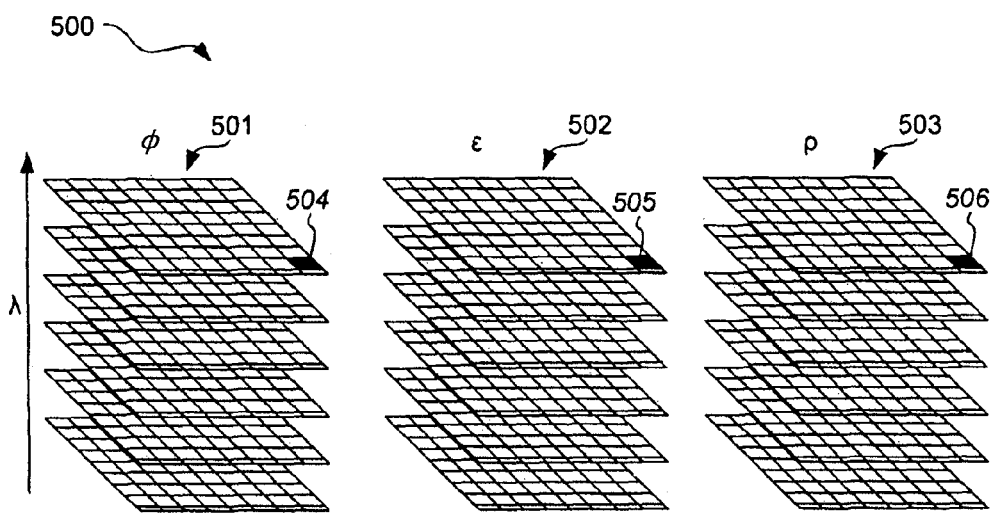
FIG. 5 illustrates a wavelength-indexed data structure.

FIG. 5 illustrates a wavelength-indexed data structure 500 after the above method has been performed for each pixel location u and each wavelength λ independently. The wavelength-indexed data structure 500 comprises a first data sub-structure 501 for storing the wavelength-indexed polarisation angles ϕ, a second data sub-structure 502 for storing the wavelength-indexed residual error ϵ and a third data sub-structure 503 for storing the wavelength-indexed degree of polarisation $\rho=I_{min}/I_{max}$. All three data sub-structures 501, 502 and 503 hold the values for all pixel locations and all wavelengths but are now independent of the filter angle. Pixel location $u_1$ at wavelength $\lambda_1$ is still highlighted in each data sub-structure at 504, 505 and 506.

In order to determine a single azimuth angle α per pixel, for each pixel a weighted average of the wavelength-indexed polarisation angles ϕ is computed, such that a polarisation angle associated with a larger residual error ϵ is assigned a smaller weight ω than a polarisation angle ϕ associated with a smaller residual error ϵ. This is achieved by using the Epanechnikov kernel such that $$\omega(u,\lambda) = \begin{cases} 1 - g(\varepsilon(u,\lambda))^2 & \text{if } \|g(\cdot)\| < 1 \\ 0 & \text{otherwise} \end{cases} \quad (4)$$

where $$g(\varepsilon(u,\lambda))^2 = \frac{\varepsilon^2(u,\lambda)}{h}$$

and h is a bandwidth parameter.

Since the azimuth angle α is a directional quantity, instead of averaging the polarisation angles ϕ directly, we estimate the mean of the sines and cosines of the polarisation angles ϕ for each pixel location as follows $$\langle \sin(\phi) \rangle_\lambda = \frac{\sum_\lambda \sin(\phi)\omega(u,\lambda)}{\sum_\lambda \omega(u,\lambda)}$$

$$\langle \cos(\phi) \rangle_\lambda = \frac{\sum_\lambda \cos(\phi)\omega(u,\lambda)}{\sum_\lambda \omega(u,\lambda)}$$

Where $\langle \cdot \rangle_\lambda$ denotes the mean value across wavelengths.

The estimated azimuth angle α at pixel u then becomes $$\alpha^*(u) = \begin{cases} \arctan\left(\frac{\langle \sin(\phi) \rangle_\lambda}{\langle \cos(\phi) \rangle_\lambda}\right) & \text{if } \langle \cos(\phi) \rangle_\lambda > 0 \\ \arctan\left(\frac{\langle \sin(\phi) \rangle_\lambda}{\langle \cos(\phi) \rangle_\lambda}\right) + \pi & \text{if } \langle \cos(\phi) \rangle_\lambda < 0 \\ \frac{\pi}{2} & \text{if } \langle \cos(\phi) \rangle_\lambda = 0 \end{cases}$$

The result is an azimuth angle α that reflects measurements for a wide range of different wavelengths and is therefore less prone to inaccuracies.

Joint Estimation of the Zenith Angle and Refractive Index

As mentioned above, the zenith θ angle can be determined by the degree of polarisation detected by the camera. The Fresnel Equation of the degree of polarisation is $$\frac{I_{min}}{I_{max}} = \frac{1 - F_\perp(u,\lambda)}{1 - F_\parallel(u,\lambda)} \quad (6)$$

$$= \left[\frac{\cos\theta(u)\sqrt{n(u,\lambda)^2 - \sin^2\theta(u)} + \sin^2\theta(u)}{n(u,\lambda)}\right]^2$$

where θ (u) is the zenith θ angle of the surface normal at location u, n(u, λ) is the material dependent refractive index of the same location at wavelength λ, and $F_\perp(u,\lambda)$ and $F_\parallel(u,\lambda)$ are the perpendicular and parallel Fresnel reflection coefficients respectively. Note that the wavelength-indexed degree of polarisation $\rho=I_{min}/I_{max}$ has been determined as described with reference to FIGS. 3 and 4 and stored as described with reference to FIG. 5.

The only unknowns in (6) are the azimuth α and the refractive index n(u, λ). Since the refractive index n(u, λ) is different for each wavelength, θ and n cannot be determined by fitting (6) to the image data captured for different wavelengths. Each layer of data sub-structure 503 in FIG. 5 for wavelength $\lambda_i$ introduces another unknown variable $n(u, \lambda_i)$. Nevertheless, the cost function for this optimisation problem can be formulated as $$E(u) = \sum_{i=1}^{K} \left[\frac{\cos\theta(u)\sqrt{n(u,\lambda_i)^2 - \sin^2\theta(u)} + \sin^2\theta(u)}{n(u,\lambda_i)} - r(u,\lambda_i)\right]^2 \quad (7)$$

where $r(u,\lambda_i)$ is the shorthand notation for $(I_{min}(u,\lambda_i)/I_{max}(u,\lambda_i))^{1/2}$ In order to overcome the problem of too many unknown variables, a further constraint can be provided on the refractive coefficient n. Cauchy's dispersion equation provides a good model for the wavelength dependence of the refractive index:

$$n(u,\lambda) = \sum_{k=1}^{M} C_1(u)\lambda^{-2(k-1)} \quad (8)$$

This dispersion equation relates the refractive index to the wavelength with coefficients $C_k(u)$, $k \in \{1, \ldots, M\}$ that are characteristic for the material. With this representation of n(u, λ) the cost function E(u) in (7) can be reparameterised as a function of M+1 variables, including the zenith θ and the dispersion coefficients $C_k(u)$, $k \in \{1, \ldots, M\}$. If the number of M dispersion coefficients is chosen such that M+1≤K, where K is the number of wavelengths, then the nonlinear least square problem can be solved numerically by standard line-search or trust-region methods in order to minimise the difference in equation (7) between the model of equation (6) and the estimated wavelength-indexed degree of polarisation.

Having obtained azimuth angle α and zenith angle θ of the surface normal vectors, the shape under study can be recovered by means of a surface integration method such as in [3]. On the other hand, the refractive index can be recovered from the dispersion equation using the dispersion coefficients $C_k(u)$ and (8).

Figure 6:
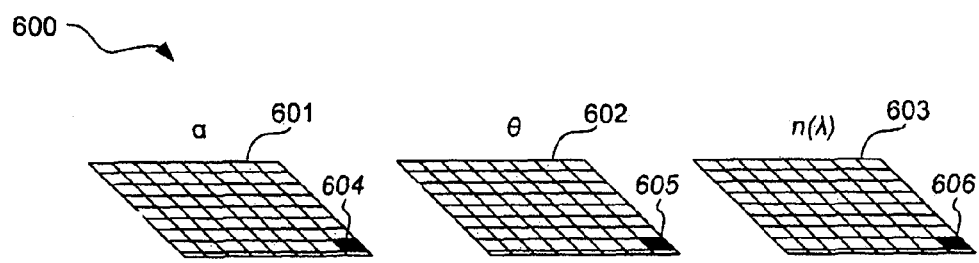
FIG. 6 illustrates the result data.

FIG. 6 illustrates the result data 600 from the above method. The result data 600 comprises values for the azimuth α 601, values for the zenith θ 602 and wavelength-dependent expressions for the refractive index n(λ) 603. As before, the pixel location $u_1$ is highlighted at 604, 605 and 606 for the values for the azimuth α 601, values for the zenith θ 602 and expressions for the refractive index n 603 respectively. Although the refractive index is dependent on the wavelength, it is shown as only one layer 603 in FIG. 6. This is because the proposed method determines an analytical expression (see equation (8)) for the refractive index for each wavelength. As a result, the refractive index is determined not only for the wavelengths for which the image data was captured but also for all wavelengths in between.

Figure 7:
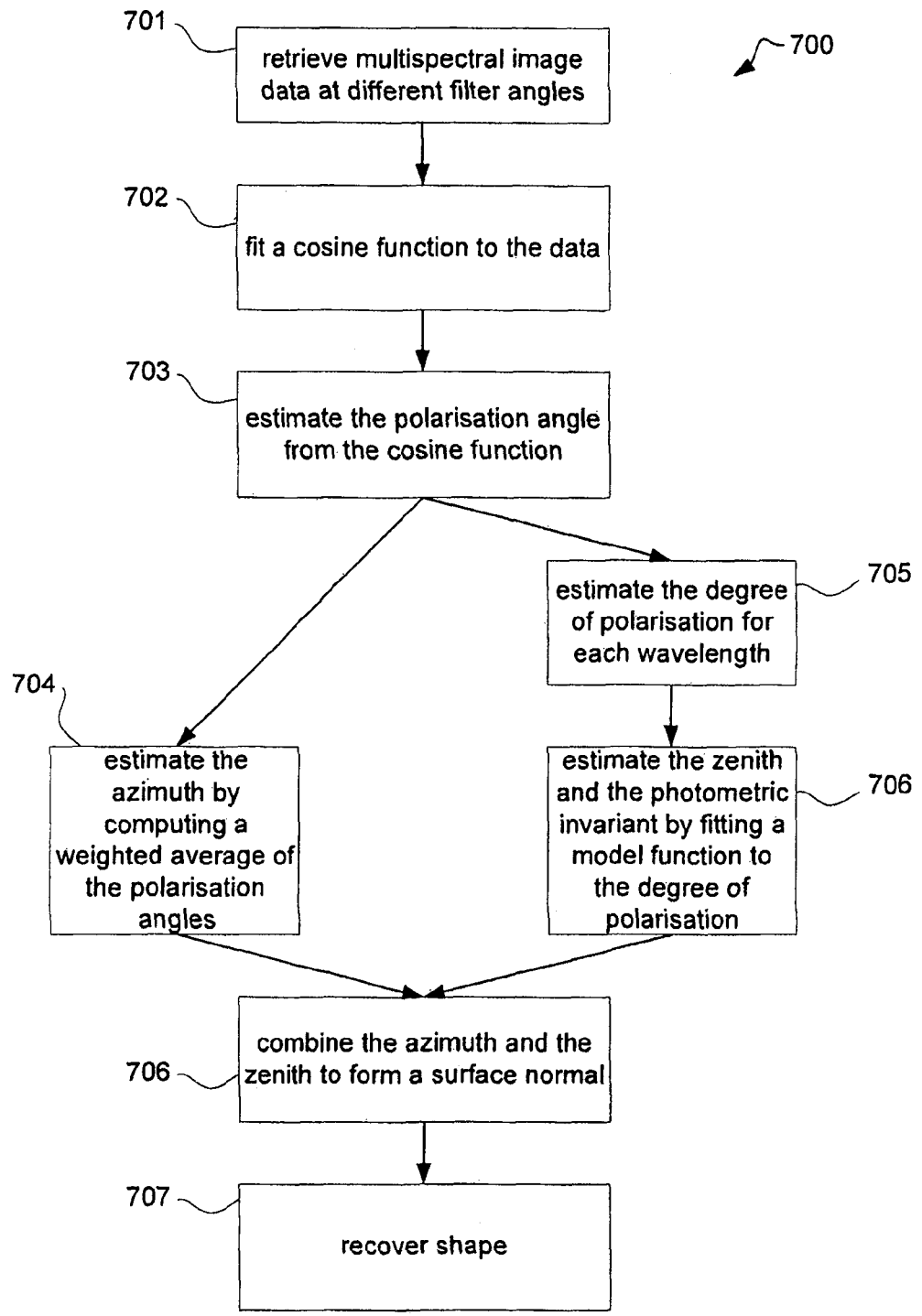
FIG. 7 illustrates a method to estimate shape information or photometric invariants of a point location of image data of a scene.

FIG. 7 illustrates a method 700 to estimate shape information or photometric invariants of a point location of image data of a scene. The photometric invariants may be the refractive index or the dispersion coefficients. First, multispectral wavelength-indexed image data is retrieved 701 for different filter angles θ. The image data comprises intensity values I for the different filter angles θ. The next step is to fit 702 a cosine function to these intensity values I. From the cosine function the polarisation angle φ is estimated 703. Steps 702 and 703 are performed for each wavelength resulting in a wavelength-indexed polarisation angle φ and from the fitting process also resulting in a wavelength-indexed residual error ε.

With the result of this fitting, an azimuth is estimated 704 by computing a weighted average of the wavelength-indexed polarisation angles for that point. The weight associated with each polarisation angle α is based on the respective residual error ε.

As an alternative or in addition to estimating the azimuth α the degree of polarisation p is estimated 705. This is also performed for each wavelength resulting in a wavelength-indexed degree of polarisation ρ(λ). A model function is then fitted 706 to the wavelength indexed degree of polarisation ρ(λ). The model function is a Fresnel Equation where the refractive index n is replaced by Cauchy's Dispersion Equation.

The method 700 then combines 706 the azimuth α and zenith θ to form a surface normal. The surface normal of all pixel locations is then integrated to recover 707 the shape.

Figure 8:
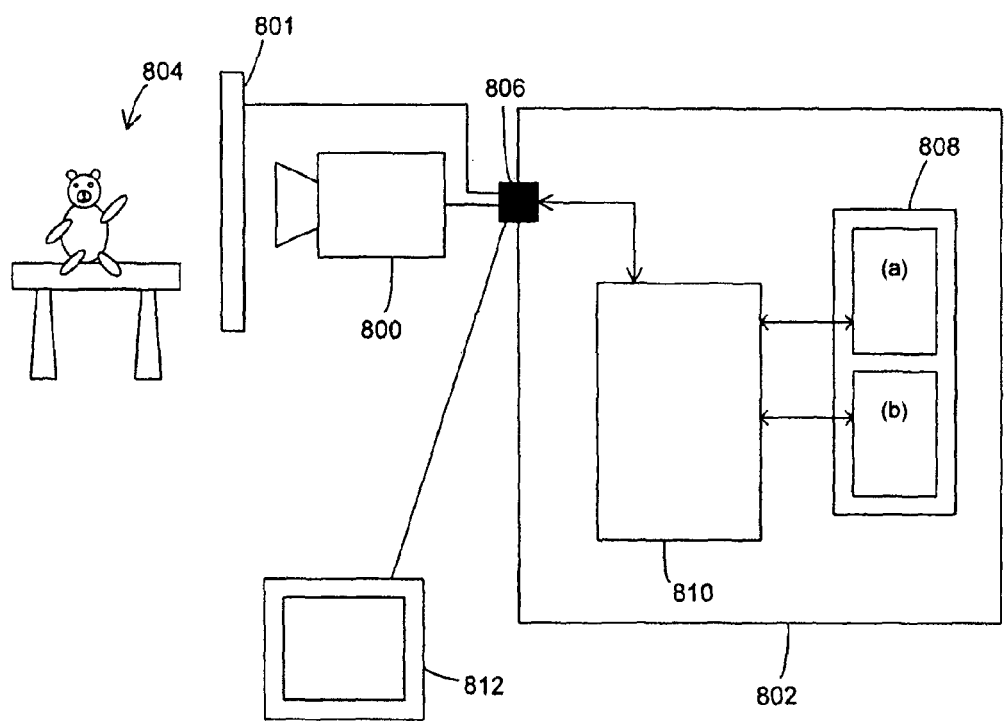
FIG. 8 is an example computer able to implement the methods described.

In the example of FIG. 8 we have an image of a teddy bear on a table and we want to automatically determine the shape and the refractive index of the teddy bear.

A computer system shown on FIG. 8 will perform this analysis. This computer system comprises a sensor 800, a rotatable polarisation filter 801 and a computer 802. In this example the sensor 800 is a hyperspectral sensor that is able to capture an image of a scene 804, in this case the teddy bear sitting on a table illuminated by an unpolarised light source (not shown). The sensor 800 may have a number of bands that balances computational costs with accuracy. The sensor 800 may have as low as four bands and as high as hundreds. The rotation of the polarisation filter 801 is controlled by computer 802 such that multiple images are captured for different filter angles, such as three to ten, and that each image is associated with the respective filter angle.

The received images and filter angles are stored in local memory 808(b) by the processor 810. The images may be stored and used in this method in the compact representation form as described in WO 2009/152583.

The processor 810 uses the software stored in memory 808(a) to perform the method shown in FIG. 7. In this sense the processor performs the method of a solver to estimate parameters of a cosine function, the method of computing a weighted average and the method of a solver of a model for the degree of polarisation for the image.

The software provides a user interface that can be presented to the user on a monitor 812. The user interface is able to accept input from the user (i.e. touch screen), such as the number of images to be taken for different filter angles or the number of parameters of the model for the refractive index. The monitor 812 displays to the user the shape information recovered by the processor performing the method. In one example, the shape information is displayed as a three-dimensional model. The monitor 812 also displays information about the refractive index.

The user input is provided to the input/out port 806 by the monitor 812. The selected image is stored in memory 808(b) by the processor 810. In this example the memory 808(b) is local to the computer 802, but alternatively could be remote to the computer 802.

The estimated surface information and photometric invariants of an image can be used in pre and post processing of the image data.

Processing of the image includes, but is not limited to:
Image editing
re-illumination, such as colour manipulation to change an image from warm to cold, or change illumination spectrum of an image to change the illumination from daylight to sunlight, or sunlight to tungsten
re-shading
re-colouring, for example to change a black and white image to colour based on the properties of a known colour set or applying the reflective properties of one image to another
light source re-positioning
material modification
highlight removal
surface rendering
material modification
Shape estimation
recovery of shape an object or scene captured in the image
Material recognition or classification
material, pattern or object recognition and classification
Hardware calibration
improve photometric calibration, such as of sensor 800 that captured the image Although in FIG. 8 the data from sensor 800 is processed by computer 802, other embodiments are also possible. For example, the sensor 800, the processor 810 and the memory 808 may be integrated within a camera. In this example, the monitor 812 may be arranged at the back of that integrated camera. Alternatively, the integrated camera may be connected to the Internet and the shape information or the photometric invariants may be transmitted from a remote camera location to a user via the Internet.

The method for estimating the shape information or photometric invariants may also be directly implemented in hardware, such as an application specific integrated circuit or a field programmable gate array. This hardware may even be integrated with the sensor 800 into a single integrated circuit.

Applications of the methods described here include to the fields of:
digital photography, such as image editing
manufacturing, such as quality and production control.
product analysis, such as determining whether a vehicle had been in an accident, and
surveillance, such as face identification and tracking.

The spectral image can be converted to a colour band representation, such as RGB (Red, Green, Blue), and in that sense the methods described here can be used to generate colour images.

It will be appreciated by persons skilled in the art that numerous variations and/or modifications may be made to the specific embodiments without departing from the scope as defined in the claims.

It should be understood that the techniques of the present disclosure might be implemented using a variety of technologies. For example, the methods described herein may be implemented by a series of computer executable instructions residing on a suitable computer readable medium. Suitable computer readable media may include volatile (e.g. RAM) and/or non-volatile (e.g. ROM, disk) memory, carrier waves and transmission media. Exemplary carrier waves may take the form of electrical, electromagnetic or optical signals conveying digital data steams along a local network or a publically accessible network such as the interne.

It should also be understood that, unless specifically stated otherwise as apparent from the following discussion, it is appreciated that throughout the description, discussions utilizing terms such as "estimating" or "processing" or "computing" or "calculating", "optimizing" or "determining" or "displaying" or the like, refer to the action and processes of a computer system, or similar electronic computing device, that processes and transforms data represented as physical (electronic) quantities within the computer system's registers and memories into other data similarly represented as physical quantities within the computer system memories or registers or other such information storage, transmission or display devices.

The present embodiments are, therefore, to be considered in all respects as illustrative and not restrictive.

REFERENCES

[1] Hecht, Eugene, Optics, 2nd Ed, Addison Wesley, 1987 [2] L. B. Wolff. Polarization vision: a new sensory approach to image understanding. Image Vision Computing, 15(2):81-93, 1997. [3] Frankot, Robert T. and Chellappa, Rama. A Method for Enforcing Integrability in Shape from Shading Algorithms. IEEE Trans. Pattern Anal. Mach. Intell., 10(4):439-451, 1988.

The invention claimed is:

1. A computer implemented method to estimate shape information and one or more photometric invariants of a location of a scene as represented in hyperspectral or multispectral image data, the image data being indexed by wavelength and polarisation filter angle, the method comprising:
(a) for each wavelength index, estimating a polarisation angle from the image data by fitting intensity information of the image data to a function of the filter angle;
(b) for each wavelength index, estimating a degree of polarisation based on intensity values of the function with reference to the estimated polarisation angle for that wavelength index;
(c) estimating the zenith of a surface normal of the scene at the location based on the estimated degree of polarisation for each wavelength index; and
(d) estimating multiple values of a photometric invariant based on the estimated degree of polarization, each of the multiple values of the photometric invariant being for a respective wavelength index, wherein estimating the multiple values of the photometric invariant is based on multiple constraints for the photometric invariant, each of the multiple constraints being a constraint for the photometric invariant for the respective wavelength index, each of the multiple constraints for the photometric invariant relates the photometric invariant to the respective wavelength index and is a function of a number of multiple constraint variables, the number of multiple constraint variables being smaller than the number of wavelength indices.

2. The computer implemented method of claim 1, further comprising:
(e) estimating the azimuth of a surface normal of the scene at the location based on the estimated polarisation angle for each wavelength index, and estimating the shape information based on the estimated azimuth.

3. The computer implemented method of claim 2, wherein step (a) comprises optimising a difference between intensity information of the image data and the function of the filter angle to estimate the polarisation angle for each wavelength index and determine a residual error for each wavelength index, and step (e) further comprises estimating the azimuth based on the polarisation angles for each wavelength index weighted by the residual error for each wavelength index.

4. The computer implemented method of claim 1, wherein steps (c) and (d) further comprise optimising a difference between a model and the estimated degree of polarisation for each wavelength index, wherein the model is based on model parameters related to the zenith and the photometric invariant.

5. The computer implemented method according to claim 4, wherein optimising the difference between a model and the estimated degree of polarisation for each wavelength index comprises determining co-efficients of a dispersion equation.

6. A non-transitory computer readable medium storing computer executable instructions that, when executed by a computer, cause the computer to perform the method of claim 1.

7. A computer system to estimate shape information and one or more photometric invariants of a location of a scene as represented in hyperspectral or multispectral image data, the image data indexed by wavelength and polarisation filter angle, the system comprising:
a processor (a) to estimate for each wavelength index a polarisation angle from the image data by fitting intensity information of the image data to a function of the filter angle, (b) to estimate for each wavelength index a degree of polarisation based on intensity values of the function with reference to the estimated polarisation angle for that wavelength index, (c) to estimate the zenith of a surface normal of the scene at the location based on the estimated degree of polarisation for each wavelength index and (d) to estimate a photometric invariant based on the estimated degree of polarisation for each wavelength index and based on a constraint for the photometric invariant for each wavelength index.

* * * * *